United States Patent
Stark et al.

(10) Patent No.: US 6,939,381 B2
(45) Date of Patent: Sep. 6, 2005

(54) TUBE SYSTEM FOR RECONSTRUCTING OF HOLLOW ORGANS

(75) Inventors: Bjorn Stark, Freiburg (DE); Alexander Bach, Freiburg (DE)

(73) Assignee: Universitatsklinikum Frieburg, Freiburg (DE)

( * ) Notice: Subject to any disclaimer, the term of this patent is extended or adjusted under 35 U.S.C. 154(b) by 94 days.

(21) Appl. No.: 10/332,871

(22) PCT Filed: Jul. 10, 2001

(86) PCT No.: PCT/EP01/07911

§ 371 (c)(1),
(2), (4) Date: Jan. 13, 2003

(87) PCT Pub. No.: WO02/04039

PCT Pub. Date: Jan. 17, 2002

(65) Prior Publication Data

US 2003/0149489 A1 Aug. 7, 2003

(30) Foreign Application Priority Data

Jul. 12, 2000 (AT) .......................................... 1203/2000

(51) Int. Cl.⁷ ............................ A61F 2/04; A61M 27/00
(52) U.S. Cl. ..................... 623/23.66; 604/544; 604/517
(58) Field of Search ................ 623/11.11, 23.64–23.68; 604/27, 43, 48, 96.01, 544, 102.1, 264, 500, 517

(56) References Cited

U.S. PATENT DOCUMENTS 5,007,897 A 4/1991 Kalb et al.
5,211,664 A * 5/1993 Tepic et al. ............... 623/16.11
5,575,815 A 11/1996 Slepian et al.

FOREIGN PATENT DOCUMENTS

WO WO92/09311 6/1992
WO WO99/22781 5/1999

OTHER PUBLICATIONS

Bach A., et al., "A New Concept for Urethral Reconstruction—Fibrin Glue as a Matrix for Autologous Urothelial Cells," Cells Tissues Organs, 2$^{nd}$ Biovalley Engineering Symposium, Freiburg, Germany, Nov. 25–27, 1999, vol. 166, No. 1.

Png, J.C.D., et al., "Principles of ureteric reconstruction," Current Opinion in Urology 2000; 10: 207–212.

International Search Report for PCT Application No. PCT/EP01/07911, issued by the European Patent Office on Jan. 21, 2002.

* cited by examiner

*Primary Examiner*—David J. Isabella
(74) *Attorney, Agent, or Firm*—Reed Smith, LLP

(57) ABSTRACT

A tube system (1) for reconstructing a hollow organ, comprising a tube (2) for draining a substance, like e.g. urine, wherein the tube (2) for draining the substance is arranged within an outer tube (5) and that the space (4) between the two tubes (2, 5) is provided for the application of cells, and wherein the outer tube (5) is formed by a membrane (5) permeable for the cells to be applied, in particular a microperforated membrane (5).

18 Claims, 1 Drawing Sheet

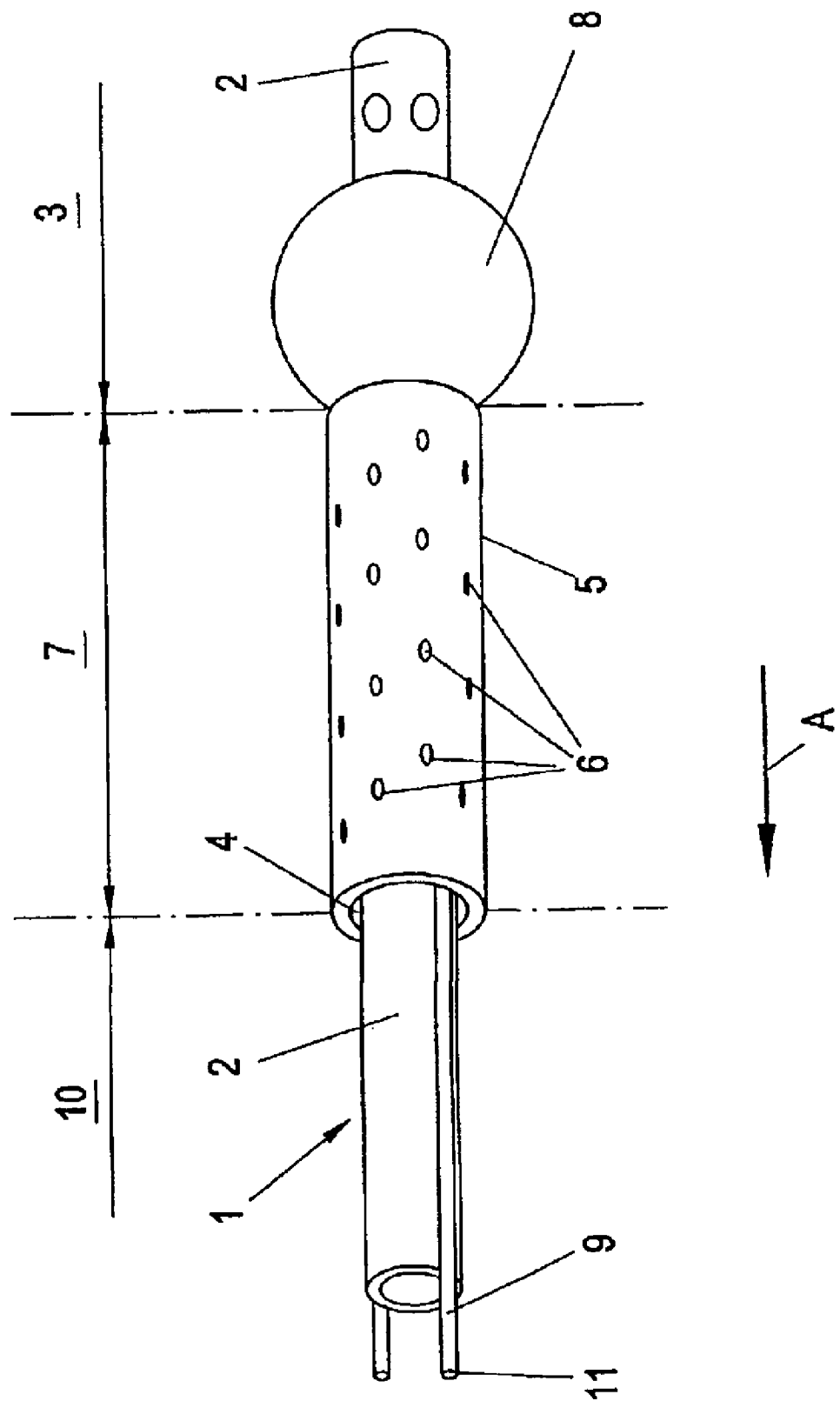

TUBE SYSTEM FOR RECONSTRUCTING OF HOLLOW ORGANS

The invention relates to a tube system for reconstructing a hollow organ comprising a tube for draining substances.

Such a tube system can be used in medicine so as to form a substitute of defective hollow organs or parts thereof occurring in case of congenital anomalies, tumour resections or other impairments which can cause disfunctioning of the organ. Such tube systems are especially useful for the formation or reconstruction of the urethra.

In reconstructing hollow organs like urethra tubes of the most varying materials have been used so far in this special field of medicine, such as synthetic materials as well as various types of tissue as free implants, vessel-containing skin parts, autologous buccal mucosa or mucosa of the bladder and epidermis cells for lining purposes. This technique, however, involves considerable complications, such as immunological rejection of the foreign matter or foreign tissue. In case of urethra linings, it has not yet been achieved to protect the underlying tissue from the aggressive action of urine. Fistulae, perforations and stenoses of the reconstructed urethras are the consequences thereof.

A new development of reconstruction techniques in connection with the formation of urethras has been presented in a contribution by Bach et al. at the 30$^{th}$ anniversary of the Deutsche Vereinigung für Plastische Chirurgie (German Association for Plastic Surgery), Sep. 15–16, 1999 at Seeon, Germany, wherein the construction of an artificial urethra by transplanting urothelial cells was illustrated. In particular, a catheter is implanted so as to cause an interconnected tubular construct formed by tissue; the catheter is then removed, and a second thinner catheter with autologous in vitro-cultured urothelial cells for lining the tissue space is inserted. A further, flexible cathether is then used to form a connection between the generated artificial urethra and the urinary bladder. In doing so it is a problem that at given time intervals (e.g. of a few weeks each), catheters must be newly inserted, which, on the one hand, is stressful for the patient and requires increased medical expenditures since several surgical interventions are necessary, and which, on the other hand, results in a considerable time delay of the entire transplantation, or reconstruction, respectively. Moreover, several different apparatuses are required, resulting in complex handling and high expenditures.

Therefore, it would be of importance to provide a remedy in order to reduce insufficient functional results and the patients' high morbidity.

Therefore, it is an object of the invention to provide a tube system of the type initially defined enabling, in an advantageous manner, a safe drainage of substances and a formation of the hollow organ using transplanted autologous cells so as to re-establish the protective function of the cells in the interior of the hollow organ.

The tube system according to the invention and of the type initially defined is characterised in that the tube for draining substances is arranged within an outer tube, and that the space between the two tubes is provided for the application of cells, and that the outer tube is formed by a membrane, in particular a micro-perforated membrane, which is permeable in respect to the cells to be applied.

In the present tube system, the inner tube arranged within the outer tube advantageously allows for a transportation of substances or fluids without thereby negatively affecting the hollow organ construct to be formed. At the same time, the space provided between the inner tube and the membrane-formed outer tube allows the tissue to generate, for which purpose, in particular, an application of appropriate protective, preferably autologous cells cultured in vitro is performed, this being done through the said membrane, from the inside to the outside. On account of this permeability, in particular of the micro-perforations, the required penetration of the cells to be applied is attained, and by migration and proliferation of these cells in the immediate vicinity, an undisturbed lining of the inner tissue space of the hollow organ with the appropriate protective cells is enabled. For this purpose it is suitable if the micro-perforations have a diameter in the order of 300 μm; with such a size the cells can penetrate, as desired, therethrough without any problem and, on the other hand, any possible clogging of the micro-perforations can be avoided.

It should be mentioned that it is already known, for instance, from WO 92/09311 A, or U.S. Pat. No. 5,575,815 A, that cells or other bioactive materials may be delivered from an outer lumen into blood or the like passing through an inner lumen of the respective catheter system. Accordingly, vascular protheses are concerned here, and it is the inner tube which is penetrable to bioactive materials.

The tube system according to the invention preferably is provided with an epithelial lining.

The inner tube of the tube system according to the invention preferably is made of silicone. Silicone is not only well suitable for medical applications, it also provides a stable tube system for an advantageous supporting function in the manner of a "splinting" of the surgical wound.

The micro-perforated membrane may be made of a natural or a synthetic polymer, such as of polylactic acid (PLA), polyglycolic acid (PGA), polyglycol-polylactic acid (PGLA), fibrin or collagen. Such membranes are tissue-tolerable, durable and resistent. It is also particularly advantageous if the membrane material is bio-absorbable.

Preferably, the tube system has a sealing so as to prevent substances to be drained from entering into the space between the tubes or into the region of the tissue formation. Accordingly, it is advantageous if the inner tube has an associated sealing member, preferably a balloon. Advantageously, the balloon is inflatable so as to allow in connection with the inner tube for a continuous drainage of the liquid, like e.g. urine from a urinary bladder in the manner of a balloon catheter.

Furthermore, it is advantageous if the space between the tubes is connected with at least one hose or tube for application of the cells, preferably in the form of a suspension. By aid of this hose, protective cells may simply be delivered into the space between the tubes, from where the cells may get through the membrane to the inner side of the hollow organ construct. For such a procedure, the hose suitable protrudes beyond the aperture outwardly directed (the orifice) for a simplest insertion of cells as possible. The hose has a substantially smaller diameter than the inner tube.

To allow a particularly efficient cell application, a syringe fitting means for injecting cells, preferably in the form of a suspension, is provided-at one end of the hose. This allows for practical handling.

Advantageously, the cells to be inserted are autologous cells, in particular urothelial cells which are cultured in vitro and are then suspended in a transportation matrix, preferably a fibrin adhesive. In doing so it is achieved that the cells are introduced through the transplant into the adjacent connective tissue space by means of the tube system of the invention without causing any rejections or other immunological disorders. In detail, it is, for instance, possible to grow and proliferate in vitro the patient's own tissue cells obtained by biopsy. The suspension in a fibrin adhesive as transportation matrix allows for gentle transportation and a reliable transfer of the in-vitro grown urothelial or, general tissue cells, respectively.

The present tube system is to be dimensioned in dependence on the shape of the hollow organ to be reconstructed, and it may, for instance, be formed as a double-lumen catheter system, with the inner lumen forming the inner tube and the outer lumen forming the outer tube.

The tube system may also contain already applied cells in the intermediate space, such as for example urothelial cells. Such embodiment is particularly advantageous if the cells are maintained in a deep-frozen state and are thawed when needed, prior to a surgical intervention, and are inserted into the urethra. Since cells are storable under deep-frozen conditions for a certain period of time, such cells can be made available at short notice together with the tube system. The removal of the endogenous cells from the patient's defective hollow organ and the subsequent in vitro cell proliferation may take place beforehand, at a preliminary examination being necessary anyway, so as to guarantee the immunological advantages when re-inserting the autologous cells.

Summing up, as advantages of the present invention it may be emphasized that a tube system or a double-lumen catheter is provided which, on the one hand, primarily can be introduced orthotopically in the course of a surgical intervention or during the reconstruction of the connective tissue portion of a hollow organ (e.g. urethra) and by which, on the other hand, a continuous drainage of substances, e.g. urine is attained under sealing, preferably by means of an inflatable balloon, with a simultaneous splinting and protection of the surgical wound being ensured. Moreover, the present tube system allows for the primary and secondary settlement of the connective tissue space surrounding the tube system with cultured autologous cells transported in a transportation matrix by way of the outer tube.

An examplary embodiment of the present invention will now be described in more detail with reference to the drawing. Here, the single drawing FIGURE gives a schematic illustration of a tube system in the form of a double-lumen catheter which is inserted for reconstructing an urethra.

In particular, the drawing shows the tube system being a double-lumen catheter 1 comprising within an inner tube 2 a closed inner lumen having a bladder-side aperture and an outer aperture for draining substances from the urinary bladder 3, as well as an outer lumen 4. This outer lumen 4 is outwardly delimited by a membrane 5 being the outer tube which is provided with micro-perforations 6. When reconstructing an urethra the area of which is schematically indicated at 7 in the drawing, this membrane 5, or outer tube, respectively, comes to lie in this urethra region 7, and cells supplied to the space between the tubes 2 and 5, i.e. to the outer lumen 4, are able to pass through the micro-perforations 6 so as to consequently initiate the formation of an inner tissue space of the urethra. On the open end of the catheter 1 which is directed towards the bladder, a sealing is provided in the form of a conventionally inflatable balloon 8 which prevents an unintended entry of urine into the region of the tissue formation, whereby a continuous emptying of the bladder 3 is enabled. This balloon 8, furthermore, prevents the system sliding out of the urethra and ensures contact to the bladder. The flow direction of the urine has been indicated by an arrow A in the drawing.

A hose or tube 9 is introduced into the space 4 between the inner tube 2 and the outer tube 5 so as to supply the space 4 with the afore-mentioned cells from the outside 10. At the outer, open end of the hose 9 located opposite of the balloon 8, i.e. at the side of the orifice, a—merely quite schematically indicated—syringe fitting means 11 is provided which ensures that the direct cell application can simply be effected by means of an injection syringe.

Via this syringe fitting means 11, thus, in-vitro cultured autologous urothelial cells are injected as a suspension in a fibrin adhesive by using the syringe (not illustrated). This facilitates an efficient, gentle cell application and consequently ensures a careful migration and settlement of the autologous urothelial cells in the interior of the urethra.

The inner tube 2 forming the inner lumen preferably consists of silicone, whereas the micro-perforated membrane 5 delimiting the outer lumen 4, in particular, is made of a natural or synthetic, bioabsorbable polymer, such as poly-lactic acid (PLA), polyglycol-poly-lactic acid (PGLA), fibrin or collagen. Likewise, the hose 9 may be made, e.g., of silicone.

The inner tube 2, together with the inflatable balloon 8, is designed as a conventional balloon catheter, and therefore, no further explanation is required.

Thus, a tube system 1 is obtained which is, on the one hand, relatively simple to handle, and which, on the other hand, constitutes an effective possibility for reconstructing, e.g. an urethra with autologous urothelial cells.

What is claimed is:

1. An urethra tube system comprising:
   an inner tube having a lumen configured to drain urine;
   an outer tube having a lumen configured and dimensioned to receive the inner tube, wherein a space is defined between the outer tube and the inner tube when the inner tube is received within the outer tube; and
   isolated cells positioned within the space defined between the inner tube and the outer tube, wherein the cells are capable of reconstructing the urethra;
   wherein the outer tube includes a micro-perforated membrane comprising a bioabsorbable permeable material to which the cells are applied.

2. The urethra tube system according to claim 1, wherein the membrane forms micro-perforations having a diameter of around 300 $\mu$m.

3. The urethra tube system according to claim 1, wherein the inner tube is comprised of silicone.

4. The urethra tube system according to claim 1, wherein the membrane is comprised of a natural polymer.

5. The urethra tube system according to claim 1, wherein the membrane is comprised of a synthetic polymer.

6. The urethra tube system according to claim 1, wherein the inner tube includes a sealing member comprising a balloon.

7. The urethra tube system according to claim 1, including a hose means extending into the space for application of the cells.

8. A The urethra tube system according to claim 7, wherein the hose means is configured for the application of cells in the form of suspension.

9. The urethra tube system according to claim 7, wherein an end of the hose is attached to a syringe fitting means.

10. The urethra tube system according to claim 1, wherein the inner tube and outer tube comprise a double-lumen catheter for drainage of urine and the simultaneous lining of the urethra with cells.

11. The urethra tube system according to claim 1, wherein the cells for lining the inner space of the urethra are disposed within the space.

12. The urethra tube system according to claim 1, wherein the cells include urothelial cells.

13. The urethra tube system according to claim 12, wherein the urothelial cells include in-vitro cultured autologous urothelial cells suspended in a transportation matrix.

14. The urethra tube system according to claim 13, wherein the transportation matrix includes a fibrin adhesive.

15. The urethra tube system according to claim 1, wherein the outer tube has a diameter of 0.8 mm to 1.5 mm, preferably 1.2 mm.

16. The urethra tube system according to claim 15, wherein the outer tube has a diameter of 1.2 mm.

17. The urethra tube system according to claim 1, wherein the inner tube has a diameter of 0.5 mm to 1.2 mm.

18. The urethra tube system according to claim 17, wherein the inner tube has a diameter of 0.8 mm.

* * * * *